United States Patent [19]
Benecke et al.

[11] Patent Number: 5,008,110
[45] Date of Patent: Apr. 16, 1991

[54] STORAGE-STABLE TRANSDERMAL PATCH

[75] Inventors: Arnold G. Benecke, Hamilton; Daniel J. Kinne, Cincinnati; Andrew J. Wnuk, Wyoming, all of Ohio

[73] Assignee: The Procter & Gamble Company, Cincinnati, Ohio

[21] Appl. No.: 269,513

[22] Filed: Nov. 10, 1988

[51] Int. Cl.⁵ .................................................. A61K 9/00
[52] U.S. Cl. ..................................... 424/448; 424/449
[58] Field of Search ................................. 424/449, 448

[56] References Cited

U.S. PATENT DOCUMENTS

| | | | |
|---|---|---|---|
| 3,742,951 | 7/1973 | Zaffaroni | 128/268 |
| 4,144,317 | 3/1979 | Higuchi et al. | 424/21 |
| 4,262,003 | 4/1981 | Urquhart et al. | 424/267 |
| 4,409,206 | 10/1983 | Stricker | 424/81 |
| 4,470,962 | 9/1984 | Keith et al. | 424/28 |
| 4,564,010 | 1/1986 | Coughlan | 128/156 |
| 4,600,001 | 7/1986 | Gilman | 128/156 |
| 4,615,699 | 10/1986 | Gale et al. | 604/897 |
| 4,627,429 | 12/1986 | Tsuk | 128/156 |
| 4,690,683 | 9/1987 | Chien et al. | 604/896 |
| 4,693,711 | 9/1987 | Bremer et al. | 604/306 |
| 4,695,277 | 9/1987 | Lauk | 604/304 |
| 4,746,509 | 5/1988 | Haggiage et al. | 424/449 |
| 4,746,515 | 5/1988 | Cheng et al. | 424/449 |
| 4,747,845 | 5/1988 | Korol | 604/368 |
| 4,751,087 | 6/1988 | Wick | 424/449 |
| 4,751,133 | 6/1988 | Szycher et al. | 428/254 |
| 4,756,314 | 7/1988 | Eckenhoff et al. | 128/760 |
| 4,756,710 | 7/1988 | Bondi et al. | 424/449 |
| 4,764,379 | 8/1988 | Sanders et al. | 424/449 |
| 4,784,857 | 11/1988 | Berry et al. | 424/449 |

*Primary Examiner*—Thurman K. Page
*Attorney, Agent, or Firm*—E. Kelly Linman; John V. Gorman; Richard C. Witte

[57] ABSTRACT

A shelf-stable device for transdermally administering an active pharmaceutical to a patient. The device includes a drug reservoir that contains the drug formulation. In one preferred embodiment of the present invention, the drug reservoir is sandwiched between an upper and a lower solvent barrier film that are made from a material such as a polyester that will not absorb the drug and/or skin permeating enhancing solvent, if any, contained within the reservoir. The drug reservoir and solvent barrier films are encapsulated within a hermetically-sealed compartment that protects the drug formulation from common environmental factors such as water vapor, oxygen, and light which can adversely affect the stability and efficacy of the drug formulation. The hermetically-sealed compartment also prevents the drug formulation from coming into contact with and possibly dissolving the adhesive used to secure the device to the patients's skin. In another particularly preferred embodiment of the present invention, the device's drug reservoir is encapsulated within a hermetically-sealed compartment that is made from solvent/environment barrier films that serve the dual functions of preventing the device's components from absorbing the drug/solvent formulation from the reservoir, and protecting the drug/solvent formulation from common environmental factors.

20 Claims, 4 Drawing Sheets

STORAGE-STABLE TRANSDERMAL PATCH

TECHNICAL FIELD

The present invention relates to a device for transdermally administering an active pharmaceutical to a patient at a substantially uniform rate over an extended period of time.

BACKGROUND OF THE INVENTION

Treating a patient with a pharmaceutically active substance is commonly performed by periodically administering a defined dose of the pharmaceutical either orally (enteral) or by inJection (parenteral). In order to assure that an effective dosage of the drug is present in the patient's body at all times, peak dosages that are much higher than the effective level usually need to be initially administered. Such a procedure undesirably increases the amount of the drug that is consumed and also increases the danger of undesirable side effects. In addition, even when a substantially excessive dosage is initially administered, there is a danger that the pharmaceutical's concentration may drop below its effective level if a subsequent dosage is delayed or omitted.

Another technique that is commonly used for administering a pharmaceutical to a patient is through intravenous infusion. While this technique generally works well in providing a sustained effective level of the pharmaceutical, it is cumbersome and typically requires close supervision by trained medical personnel. Consequently, intravenous infusion generally requires the patient to be hospitalized with the associated expense and inconvenience.

Techniques and devices have also been developed for administering pharmaceuticals at therapeutic levels and rates by absorption through a patient's skin. Such delivery devices, which are now commercially available for nitroglycerin and other pharmaceuticals and include transdermal or transmucosal patches or bandages, implants, osmotic devices and the like, are very useful in continuously administering a medication at a relatively constant rate. These devices typically include a pharmaceutical-containing reservoir enclosed by a membrane through which the drug diffuses at a controlled rate. The device is typically attached either adhesively or mechanically to the patient's skin, and the drug diffuses from the device and permeates the outer sublayers of the patient's skin until it is absorbed into the bloodstream of the dermis capillary network. Once the drug enters the bloodstream, it is carried throughout the patient's entire body.

While such transdermal delivery devices work well for some pharmaceuticals such as nitroglycerine, conventional transdermal delivery devices have not proved to be suitable for many other important drugs. Specifically, the absorption rate or flux through skin for some pharmaceuticals from conventional devices has been found to be too slow to provide an effective dosage unless the size of the transdermal patch is excessively large. For example, in the case of large molecular weight drugs such as buprenorphine, which is a lipophilic opioid analgesic (see U.S. Pat. No. 3,433,791, which is incorporated herein by reference), it has been found that the drug will not readily permeate a patient's skin at a therapeutic rate if a reasonably-sized patch is used unless the skin is "softened" by using a skin permeation enhancing agent. More specifically, it has been found that the skin permeation rate for large molecular weight drugs such as buprenorphine can be significantly increased if the drug is mixed with a permeation enhancing agent such as a polar solvent material selected from the group consisting of $C_3$-$C_4$ diols, $C_3$-$C_6$ triols, and mixtures thereof; and/or a polar lipid material selected from the group consisting of fatty acids, fatty alcohols, fatty alcohol esters, fatty acid esters, and mixtures thereof. Even more specifically, it has been found that the skin permeation rate for large molecular weight drugs such as buprenorphine can be significantly raised if the drug is mixed with a permeation enhancing agent such as propylene glycol, which is basically a polar $C_3$ diol; and/or methyl laurate and methyl caprylate, which are basically lipophilic fatty acid esters.

Many previous transdermal drug delivery devices such as those disclosed in U.S. Pat. Nos. 4,564,010 to Coughlan et al. and 4,262,003 to Urquhart et al. are constructed from common packaging materials such as polyethylene and polypropylene, which are relatively inexpensive, easy to handle, and easy to seal. It has been found that such packaging material can be used to contain a diol-based skin permeation enhancer such as propylene glycol with relative ease. However, significant problems result when these same materials are used to contain a lipid component such as methyl laurate or methyl caprylate, which in some instances may be present in amounts ranging from about 1% to about 40% by weight of the total drug formulation. Specifically, hydrophobic polymers such as common polyolefins tend to readily absorb lipophilic solvents from the diol. Accordingly, depending on the drug/skin permeation enhancer formulation, the loss of the lipophilic solvent can significantly decrease the drug's solubility in the formulation and thereby cause the drug to precipitate out while the patch is in storage or during use. In addition, the solvent's loss can significantly reduce the drug flux or absorption rate through the patient's skin. Finally, the solvent entering the packaging material can significantly alter the material's physical properties which can catastrophically impact the integrity of the overall patch structure.

Additional research has shown that common environmental factors such as the presence of moisture, oxygen, and light can adversely affect the stability and efficacy of some drugs and skin permeation enhancers, which in turn can significantly impact the storage stability or shelf life of the transdermal device. For example, it has been found that the solubility of buprenorphine and the lipophilic solvents in some skin permeation enhancers such as propylene glycol decreases significantly if the formulation absorbs even a very small fraction of water. It is also been found that some drugs such as buprenorphine can degrade when exposed to light. Most prior drug delivery device architectures do not specifically address the objective of protecting the drug formulation from common environmental factors.

Most prior transdermal drug delivery devices use a dermatologically-acceptable, pressure-sensitive adhesive to secure the device to a patient's skin. In many of these structures, the drug formulation is allowed to freely come into contact with the adhesive examples of which include U.S. Pat. Nos. 3,742,951 to Zaffaroni; 4,144,317 to Higuchi et al.; 4,262,003 to Urquhart et al.; 4,690,683 to Chien et al.; and 4,764,379 to Sanders et al. However, it has been found that many of these adhesives might absorb some skin permeation enhancing agents such as propylene glycol. In addition, it has been found that lipophilic solvents such as methyl laurate and methyl caprylate will swell and even dissolve many adhesives, particularly silicones, polyisobutylenes, and acrylic-based adhesives. Accordingly, many prior transdermal devices are not suitable for containing some types of drug/skin permeation enhancer formulations.

In light of the above, the principal object of the present invention is to provide a transdermal drug delivery system that will uniformly administer a pharmaceutical to a patient in need of such treatment.

Another principal object of the present invention is to construct a transdermal drug delivery device that includes various barrier materials that will not significantly absorb the pharmaceutical and/or a skin permeation enhancer contained therewithin thereby significantly increasing the device's stability and shelf-life.

A further object of the present invention is to construct a transdermal drug delivery device that is made from barrier materials that will significantly increase the shelf life of the device by protecting the drug and/or skin permeation enhancer from common environmental factors such as moisture, oxygen, and light.

Another object of the present invention is to construct a transdermal drug delivery device such that the drug formulation is not exposed to the adhesive used to maintain the device on a patient's skin.

SUMMARY OF THE INVENTION

Transdermal drug delivery devices of the present invention are particularly useful for containing drugs and/or solvents that are not compatible with common packaging materials such as polyolefins or commonly-used pressure-sensitive adhesives. In addition, transdermal devices of the present invention are particularly useful for containing drugs and/or solvents whose stability and efficacy over an extended period of time can be negatively affected if the drug formulation is exposed to common environmental factors such as moisture, oxygen, and light.

In one preferred embodiment of the present invention, the transdermal drug delivery device includes a lower subassembly that holds a drug reservoir, and an upper subassembly. The drug reservoir, which contains the drug formulation, is sandwiched between an upper solvent barrier film and a lower solvent barrier film. These solvent barrier films are preferably made from a material such as a polyester that will not absorb the drug formulation and volatile solvents contained within the reservoir to a significant degree.

The drug reservoir and upper and lower solvent barrier films are hermetically sealed within a protective compartment having a top cover and a bottom cover. The compartment's bottom cover is attached to an adhesive-coated coverstock while the compartment's top cover is attached to a release liner. The bottom surface of the release liner is in contact with the coverstock's adhesive layer that extends beyond the compartment's bottom cover.

In use, the user peels the device's upper subassembly away from the lower subassembly, which breaks the compartment hermetic seal and exposes the drug reservoir. The lower subassembly is then applied to the patient's skin and firmly held in place by the coverstock's adhesive coating.

In another particularly preferred embodiment of the present invention, the device includes a drug reservoir that is hermetically sealed within a compartment comprised of an upper solvent/environment barrier film and a lower solvent/environment barrier film. The device's upper solvent/environment barrier film is attached to a release liner while the device's lower solvent/environment barrier film is attached to an adhesive-coated coverstock. In use, the user peels the release liner from the coverstock which breaks the hermetic seal between the upper and lower solvent/environment barrier films and exposes the drug reservoir.

BRIEF DESCRIPTION OF THE DRAWINGS

While the specification concludes with claims that particularly point out and distinctly claim the subject matter regarded as forming the present invention, it is believed that the invention will be better understood from the following detailed description with reference to the drawings in which:

DETAILED DESCRIPTION OF THE INVENTION

Figure 1:
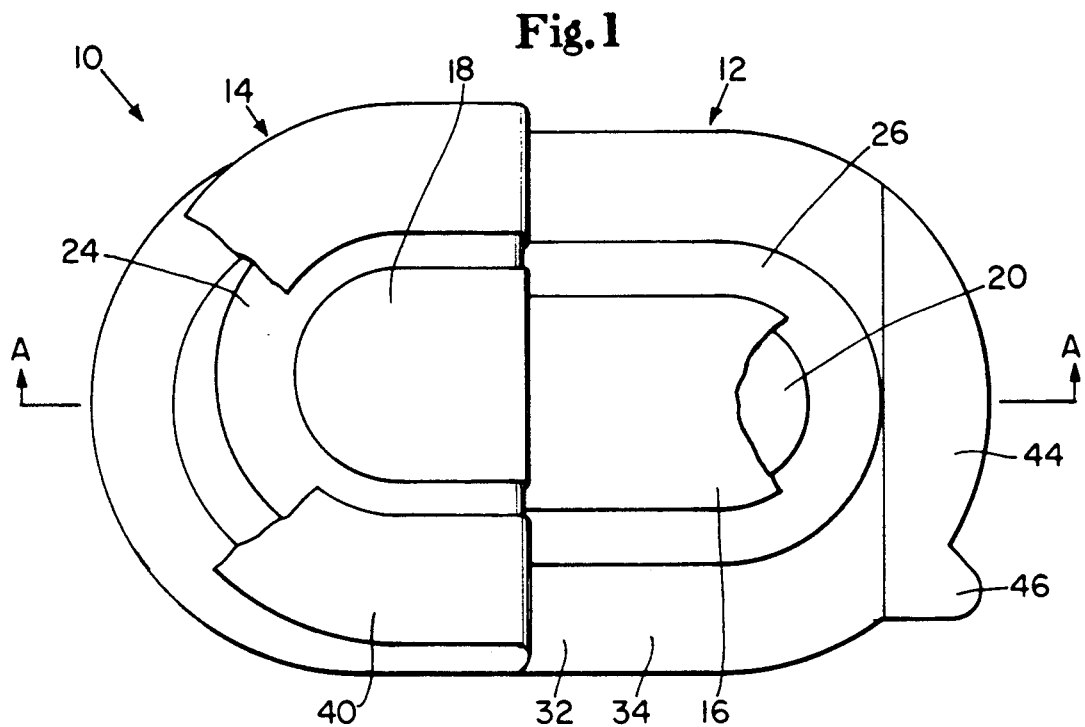
FIG. 1 is a schematic, perspective view of a preferred embodiment of a transdermal drug delivery device of the present invention shown with its upper subassembly partially peeled away from its lower subassembly and with various layers of each partially cut away to show greater detail.
Figure 2:
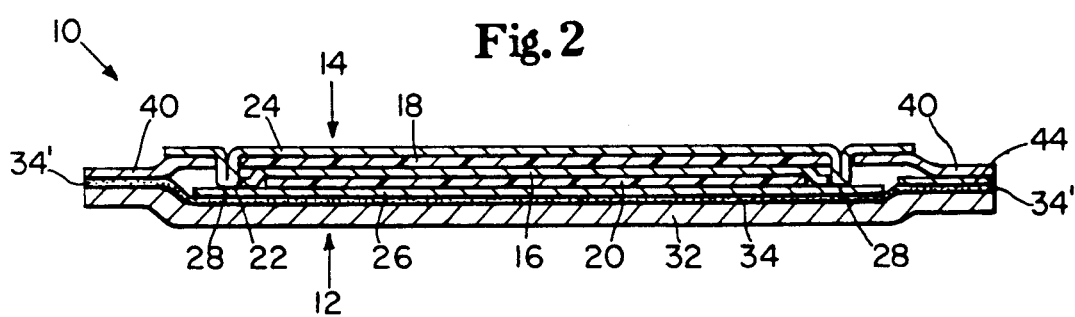
FIG. 2 is a schematic, cross-sectional view of the transdermal drug delivery device illustrated in FIG. 1 taken along section line A—A except that the device is shown with its upper and lower subassemblies hermetically sealed together.

It should be noted that although the following detailed description and illustration are generally directed to a transdermal drug delivery device for containing a drug such as buprenorphine and skin permeation enhancers such as propylene glycol, methyl laurate, and methyl caprylate, it is to be understood that the present invention may be applied with equal facility in containing other types of drugs with or without other permeation enhancers. As used herein, the term "drug" or "pharmaceutical" is intended to mean a biologically active agent, compound, or composition of matter that is administered to a patient for the purpose of providing some beneficial or therapeutic effect. The term "patient" is intended to mean any form of life, including a human, that has an outer skin and an internal blood circulation system. The terms "inner" and "outer" used in describing various surfaces are referenced with respect to the device's reservoir while the terms "upper" and "lower" and "top" and "bottom" are referenced with respect to the drawings. Finally, the terms "transdermal drug delivery device," "patch," and "bandage" are used synonymously throughout.

Referring to the drawings wherein the same numeral is used to indicate common components, FIGS. 1, 2, 3, and 4 illustrate various views of a transdermal drug delivery device of the present invention generally indicated as 10 that includes lower subassembly generally indicated as 12, and upper subassembly generally indicated as 14. Lower subassembly 12 includes drug matrix or reservoir 16 that provides the void volume necessary to hold the drug formulation in place during storage and also after device 10 has been opened and applied to a patient's skin. In addition, reservoir 16 also provides the important functions of (1) containing the drug formulation in use on the patient's skin so that the drug does not migrate into the perimeter adhesive area of the device; (2) retaining the drug formulation such that only a small fraction clings to upper subassembly 14 when the device is opened by peeling upper subassembly 14 away from lower subassembly 12; and (3) providing an inert matrix that will not absorb large quantities of the drug or solvent which otherwise would negatively impact the efficacy of the device.

In the particularly preferred embodiment of the present invention, reservoir 16 carries a safe and effective amount of buprenorphine mixed with a skin permeation enhancing agent comprised of (a) a polar solvent material selected from the group consisting of $C_3$–$C_4$ diols, $C_3$–$C_6$ triols, and mixtures thereof; and (b), a polar lipid material selected from the group consisting of fatty alcohols, fatty acids, fatty alcohol esters, fatty acid esters, and mixtures thereof, wherein the polar solvent material and the polar lipid material are present in a weight ratio of solvent material/lipid material of from about 60:40 to about 99:1. Preferably, the polar solvent material is propylene glycol, and the polar lipid material is an ester of a $C_8$–$C_{12}$ fatty alcohol or fatty acid such as methyl laurate or methyl caprylate, with the ratio of polar solvent material to polar lipid material being from about 90:10 to about 99:1. As used above, the phrase "safe and effective amount" is intended to mean the quantity of a component that is sufficient to yield a desired therapeutic response without undue adverse side effects such as toxicity, irritation, or allergic response commensurate with a reasonable benefit/risk ratio. The safe and effective amount will obviously vary depending on such factors as the particular condition or malady needing treatment, the patient's physical condition, the treatment's duration, the nature of concurrent therapy if any, and the specific formulation being used.

In the particularly preferred embodiment of the present invention, drug reservoir 16 is made from a spunbonded (nonwoven) polyester such as style number 2011 available from Reemay, Inc., P.O. Box 511, Old Hickory, Tenn., USA having a basis weight of 23 $g/m^2$ and an average thickness of 6.5 mils (0.17 mm). Other materials suitable for making drug reservoir 16 include, but are not limited to, woven and non-woven fabrics, tissues, scrims, foams, porous membranes, fibrous batting (gauze, cotton, etc.), apertured three-dimensionally expanded formed films such as those disclosed in commonly-assigned U.S. Pat. Nos. 3,929,135 and 4,342,314, which are incorporated herein by reference; and other porous materials capable of holding a liquid or gel formulation in intimate contact with skin. Reservoir 16 can also take the form of a homogeneous or heterogeneous suspension of the drug and skin permeation enhancing solvents in adhesives, adhesive and non-adhesive gels, or other polymeric matrices such as natural or synthetic rubbers, thermoplastic and thermosetting polymers, hydrophilic gels, and water soluble polymers. The drug can also be mixed with a thickening or gelling agent such as hydroxypropyl cellulose to help hold the formation in place when device 10 is opened. Other suitable gelling agents include particulate and polymeric thickeners such as guar gum, methylcellulose, methylhydroxypropyl cellulose, polypropyl cellulose, starches, carboxypolymethylene, ethylene maleic anyhdride, polyacrylamide, and poly(methylvinylether-maleic anhydride). The drug is dispersed throughout matrix or reservoir 16 at a concentration preferably in excess of saturation, the amount of excess being a function of an intended useful life of the system.

It is contemplated that any drug which may be transdermally applied to a patient is suitable for use as the drug to be applied via drug reservoir 16. It will also be appreciated that the drug will not only be in the form of the pure chemical compound, but also in admixture with other drugs and/or other ingredients that are compatible with the desired objective. Thus, simple pharmacologically acceptable derivatives of the drug such as ethers, esters, amides,-acetals, salts and the like may be used.

The scope of the present invention contemplates the use of a membrane (not shown) stretched across the upper surface of reservoir 16. For example, if the drug dispersed with reservoir 16 readily permeates skin, i.e., the drug inherently has a high skin flux, then a rate-controlling membrane such as those well-known in the art can be attached to the upper surface of reservoir 16. Alternatively, if the drug has a low skin flux, then a nonrate-controlling membrane can be attached to the upper surface of reservoir 16 for the purpose of holding the drug formulation in place and also to minimize the amount of the drug that is lost from reservoir 16 when upper subassembly 14 is peeled away from lower subassembly 12.

Still referring to FIGS. 1, 2, 3, and 4, reservoir 16 is sandwiched between upper solvent barrier film 18 and lower solvent barrier film 20. The term "solvent barrier film" is intended to mean a material that does not absorb the drug and/or skin permeation enhancing agent found in reservoir 16 to a substantial degree, an example of which includes polyester such as polyethylene terephthalate (PET). In addition, sheet barrier films 18 and 20 are preferably made from a non-stick material which acts as a release liner that minimizes the amount of the drug formulation contained in reservoir 16 that will adhere to upper solvent barrier film 18 when upper subassembly 14 is peeled away from lower subassembly 12 and discarded as will be more fully explained later. Upper solvent barrier film 18 and lower solvent barrier film 20 may be composed of the same or different material(s). Preferably, upper solvent barrier film 18 is modified, e.g., fluorinated, to provide an inert, nonwetting surface to further reduce the amount of drug formulation loss when patch 10 is opened.

In the preferred embodiment of the present invention, upper solvent barrier film 18 and lower solvent barrier film 20 are made from a laminate comprised of a layer of fluorinated polyester as the inner reservoir-contacting surface such as Scotchpak ® 1220 available from the Minnesota Mining and Manufacturing Company (3M) Health Care Specialties, and an outer layer of a heat-sealable material such as a polyolefin. Other materials that can be used for upper and lower solvent barrier films 18 and 20 include, from inner layer to outer layer, nylon/polyolefin, styrene acrylonitrile/polyolefin, ethylene vinyl alcohol copolymer (EVOH)/polyolefin, rubber modified acrylonitrile methyl acrylate copolymer (Barex ®)/polyolefin, polyvinylidine chloride copolymer (Saran ®)/polyolefin, and polychlorotrifluoroethylene copolymer (Aclar ®)/polyolefin.

Reservoir 16, upper solvent barrier film 18, and lower solvent barrier film 20 are encapsulated within hermetically-sealed compartment 22 (FIGS. 2 and 3) which comprises top cover 24 and bottom cover 26 which are sealed, preferably heat-sealed, to one another in seal area 28 adjacent to their peripheral edges. In the preferred embodiment of the present invention, top cover 24 and bottom cover 26 are made from a laminate comprised of an outer heat-sealable layer such as a polyolefin, an intermediate environment barrier layer such as a polyester, metal foil, or metallized polyester, and an inner heat-sealable polyolefin layer. The term "environment barrier layer" is intended to mean a material that is substantially impermeable to such common environmental factors such as water vapor and oxygen. Other materials suitable for the environment barrier layer of top cover 24 and bottom cover 26 include a metal foil such as aluminum, polyvinylidine chloride copolymer (Saran ®), Barex ®, nylon, EVOH, and Aclar ®.

Hermetically-sealed top cover 24 and bottom cover 26 cooperate in providing the important functions of (1) protecting the drug formulation carried by reservoir 16 from common environmental factors such as moisture (water vapor), oxygen, and light, all of which either collectively or individually can adversely affect the stability and/or efficacy of the drug formulation; (2) establishing a hermetic seal that can be easily broken when the device is ready to be used on a patient; (3) maintaining the drug formulation separate from the device's perimeter adhesive during storage; and (4) preventing the drug formulation from permeating and being lost into other components of device 10. The inner heat-sealable layer of bottom cover 26 provides a surface to which the outer peripheral edge of reservoir 16 can be conveniently attached, for example, by heat-sealing the two together. This same inner polyolefin layer of bottom cover 26 also provides a surface to which the outer heat-sealable layer of lower solvent barrier film 20 can be attached, for example, by heat-sealing the two together preferably in the entire area where the inner surface of bottom cover 26 and lower solvent barrier film 20 are in contact with one another to provide a strong bond therebetween. Similarly, the inner heat-sealable layer of top cover 24 is attached to the outer heat-sealable layer of upper solvent barrier film 18, for example, by heat-sealing, preferably in the entire area where these two layers are in contact with one another to provide a strong bond therebetween.

Transdermal device 10 also includes adhesive-coated backing sheet or coverstock 32 that is secured, e.g., adhesively, to the bottom surface of bottom cover 26 of hermetic compartment 22 with adhesive layer 34. Of particular significance is that hermetically sealed compartment 22 prevents the drug formulation contained within reservoir 16 from coming into contact with adhesive layer 34 on coverstock 32. Coverstock 32 provides the primary means for attaching device 10 to a patient's skin. Coverstock 32 may be made from a wide variety of occlusive or non-occlusive materials that include, for example, polymeric films such as polyvinyl chloride (PVC), polyethylene (PE), polypropylene (PP), polyurethane, ethylene vinyl acetate copolymer, and polyesters; flexible foams such as PVC, PE, and polyurethane; woven and non-woven fabrics; metal foils; and paper, cellophane, and cellulose derivatives. The material selected for coverstock 32 is preferably flexible enough to permit it to readily conform to the shape of the body surface area to which device 10 is to be applied.

Any of the well-known dermatologically-acceptable, pressure-sensitive adhesives can be used as adhesive coating 34 on coverstock 32. Exemplary adhesives include silicones, polyisobutylene, and acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, vinylacetate, N-branched alkyl maleamic acids wherein the alkyl group has 10 to 24 carbon atoms, glycol diacrylates, or mixtures of these. Other examples of acceptable adhesives include those based on natural or synthetic rubbers such as silicone rubber, styrene-butadiene, butyl, neoprene, polybutadiene, polyisoprene, and polyurethane elastomers; vinyl polymers, such as polyvinylalcohol, polyvinyl ethers, polyvinyl pyrrolidone, and polyvinylacetate; cellulose derivatives such as ethyl cellulose, methyl cellulose, nitrocellulose, and carboxymethyl cellulose; and natural gums such as guar, acacia, karaya, pectins, starch, dextrin, albumin, gelatin, casein, etc. The adhesives may be compounded with tackifiers and stabilizers as is well known in the art.

Figure 3:
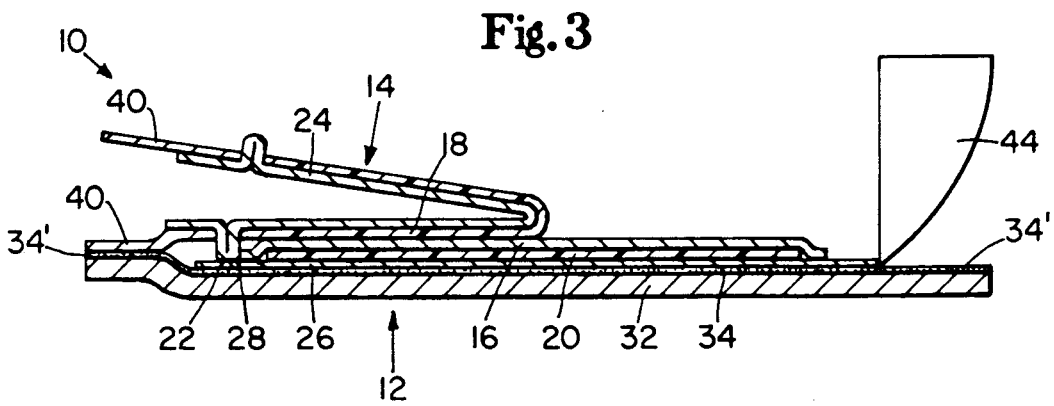
FIG. 3 is a schematic, cross-sectional view of the transdermal drug delivery device illustrated in FIG. 1 taken along section line A—A with the device's release tab shown partially peeled away from the device's lower subassembly.
Figure 4:
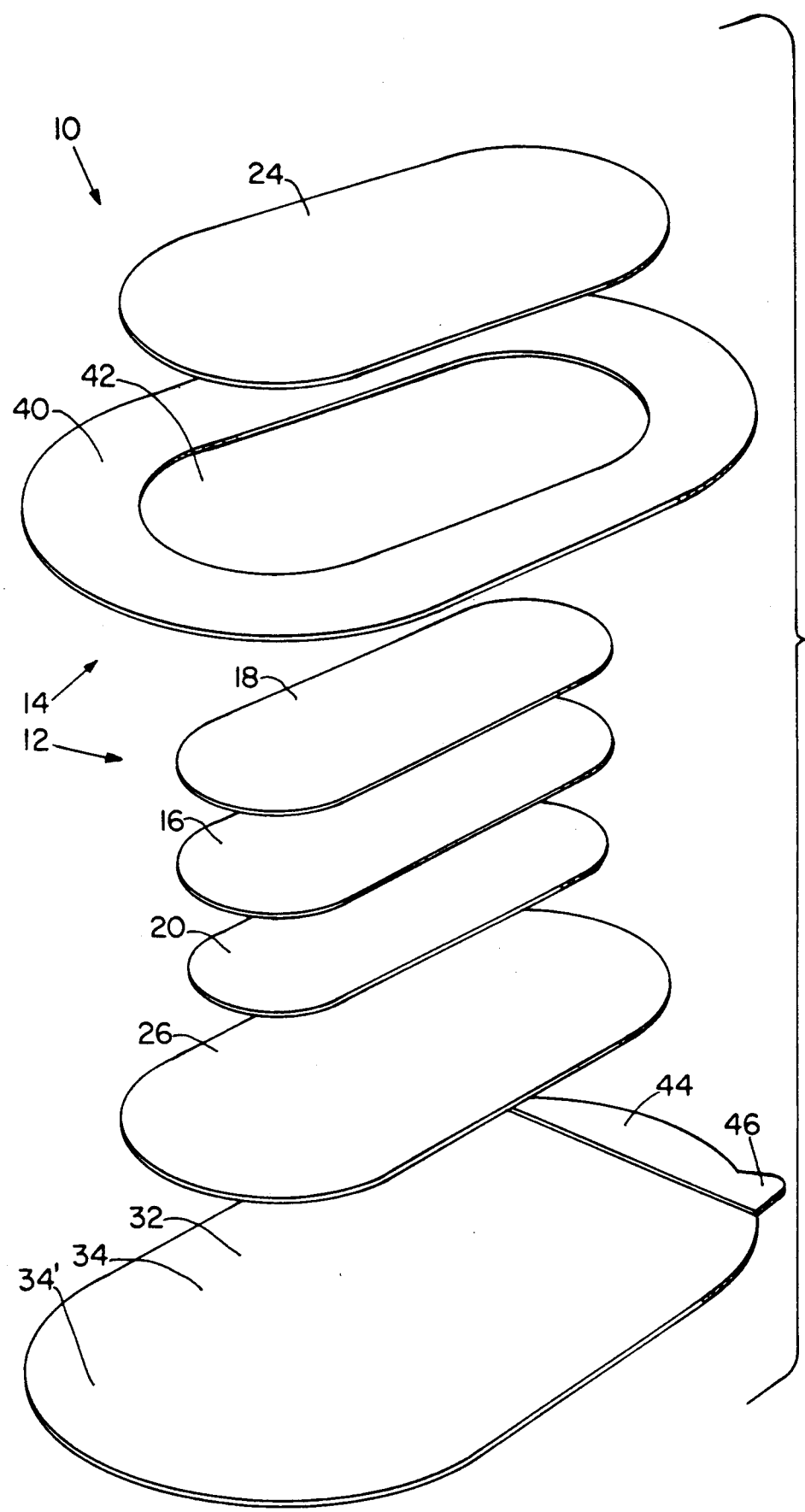
FIG. 4 is a schematic perspective, exploded view of the transdermal drug delivery device illustrated in FIGS. 1, 2, and 3.
Figure 5:
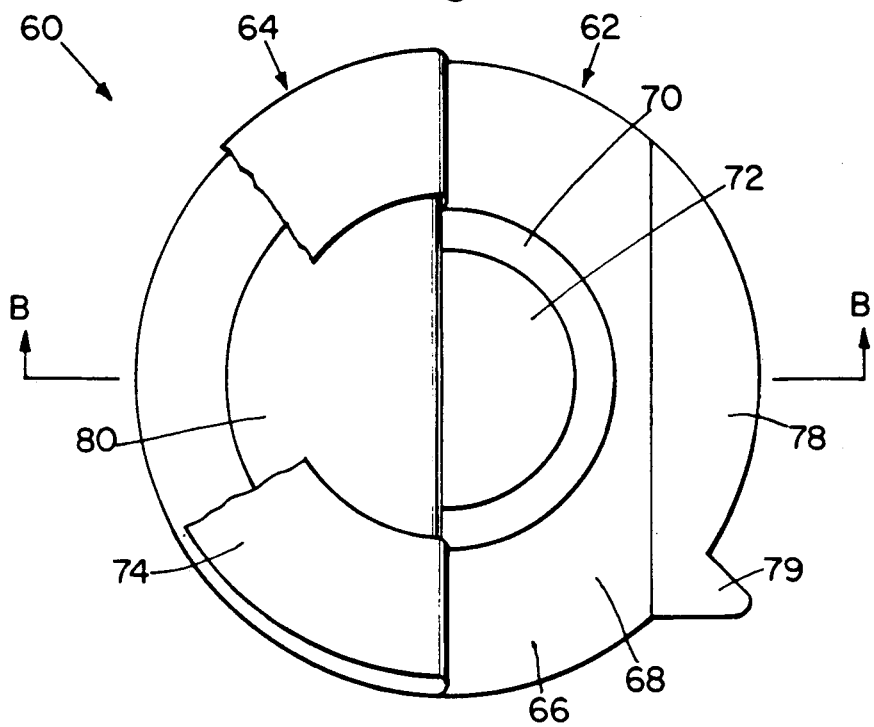
FIG. 5 is a schematic, perspective view of another particularly preferred embodiment of a transdermal drug delivery device of the present invention shown with its upper subassembly partially peeled away from its lower subassembly and with various layers of each partially cut away to show greater detail.

Still referring to FIGS. 1, 2, 3, and 4, device 10 also includes release liner 40 whose upper surface is attached to the bottom surface of top cover 24 preferably by heat-sealing the two together in their areas of overlap. As best seen in FIG. 3, release liner 40 is preferably provided with aperture or window 42 through which top cover 24 extends to allow top cover 24 and bottom cover 26 of compartment 22 to be hermetically sealed to one another at seal 28. The bottom surface of release liner 40 lying outside of seal 28 is in contact with the exposed adhesive layer 34' (FIGS. 2 and 3) on the upper surface of coverstock 32 lying outside the perimeter of bottom cover 26. Release liner 40 can be made from a wide variety of materials such as paper, waxed paper, or preferably silicone-coated kraft paper. A second, smaller piece of release liner or tab 44 is preferably interposed between release liner 40 and exposed adhesive layer 34' at one peripheral margin of device 10. Release tab 44, which also preferably includes grasping portion 46, provides an area where the user can easily start a separation (peel) between release liner 40 and coverstock 32.

In use and with reference to FIG. 3, the user inserts his or her fingers between release liner 40 associated with upper subassembly 14, and release tab 44 associated with lower subassembly 12. Then, while having a firm grasp of upper subassembly 14 in one hand and lower subassembly 12 in the other, the user gently peels the two subassemblies away from each other. In the process, hermetic seal 28 between top cover 24 and bottom cover 26 of compartment 22 is gradually broken until upper subassembly 14 is fully separated from lower subassembly 12 and reservoir 16 is exposed. Finally, the user grasps portion 46 of release tab 44 and peels tab 44 away from lower subassembly 12 as shown in FIG. 3, thereby fully exposing adhesive coating 34' around the perimeter of coverstock 32. After subassemblies 12 and 14 have been separated from one another as just described, the user disposes of upper subassembly 14 in a proper manner and applies lower subassembly 12 directly to the patient's skin in an area that is preferably free of hair, wrinkles, creases, or folds. Various locations on the torso such as the flank or shoulder provide suitable sites.

Those skilled in the art will now appreciate that transdermal drug delivery device 10 of the present invention is significantly different and superior to previous devices. Specifically, the transdermal patch of the present invention includes a hermetically sealed compartment that is preferably lined with a solvent barrier film so as to substantially prevent the drug formulation contained within the device from being absorbed by the device's other components or dissolving the device's other components, thereby significantly extending the storage stability and efficacy of the device. In addition, the hermetically sealed compartment and environment barrier films used in the present invention substantially protect the device's drug formulation from the adverse effects of common environmental factors such as moisture, oxygen, and light during storage, thereby also significantly extending the storage stability and efficacy of the device.

FIGS. 5, 6, 7, and 8 illustrate various views of another particularly preferred transdermal drug delivery device of the present invention generally indicated as 60 that includes lower subassembly generally indicated as 62, and upper subassembly generally indicated as 64. Lower subassembly 62 includes coverstock 66 which is preferably made from PVC foam or any of the other suitable materials from which previously-described coverstock 32 of patch 10 can be made. The upper surface of coverstock 66 is coated with adhesive layer 68 which similarly can be any one of the dermatologically-acceptable, pressure-sensitive adhesives as previously described in association with patch 10.

Lower subassembly 62 of patch 60 also includes lower solvent/environment barrier film 70 whose lower surface is in intimate contact with adhesive layer 68 of coverstock 66, thereby providing a strong bond therebetween. The term "solvent/environment barrier film" is intended to mean a material that does not absorb the drug and/or skin permeation enhancer found in reservoir 72 to a substantial degree and which is substantially impermeable to environmental factors such as moisture and oxygen. Drug reservoir 72, which contains the devices drug formulation and can be made from the same material as reservoir 16 of patch 10 such as a PET non-woven, is attached to the upper surface of lower barrier film 70 by, for example, heat-sealing the two together. As with previously-described transdermal device 10, the scope of the present invention contemplates the use of a rate-controlling or nonrate-controlling membrane (not shown) stretched across the upper surface of reservoir 72.

Upper subassembly 64 includes release liner 74, which is preferably made from silicone-coated kraft paper, that is provided with aperture or window 76. The bottom surface of release liner 74 is in contact with portion 68' of adhesive 68 that lies on the upper surface of coverstock 66 outside the perimeter of lower solvent/environment barrier film 70. A second small piece of release liner or tab 78 is preferably interposed between release liner 74 and exposed adhesive layer 68' at one peripheral margin of patch 60. Release tab 78, which preferably includes grasping portion 79, provides an area where the user can easily start a separation (peel) between release liner 74 and coverstock 66.

Figure 6:
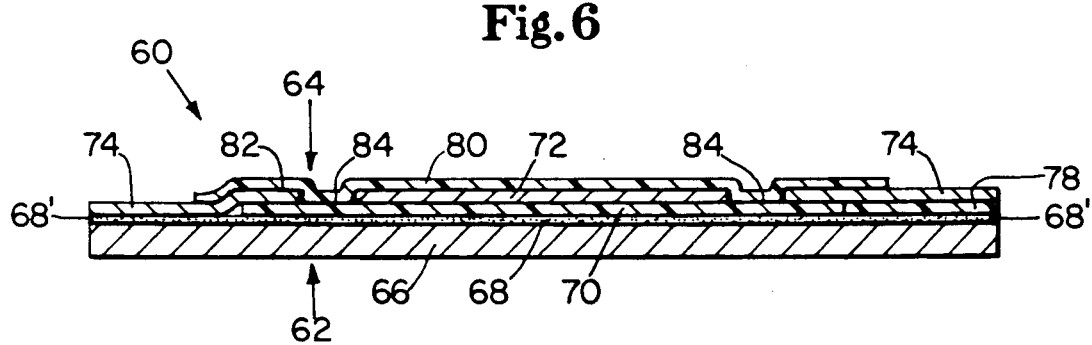
FIG. 6 is a schematic, cross-sectional view of the transdermal drug delivery device illustrated in FIG. 5 taken along section line B—B except that the device is shown with its upper and lower subassemblies hermetically sealed together.
Figure 7:
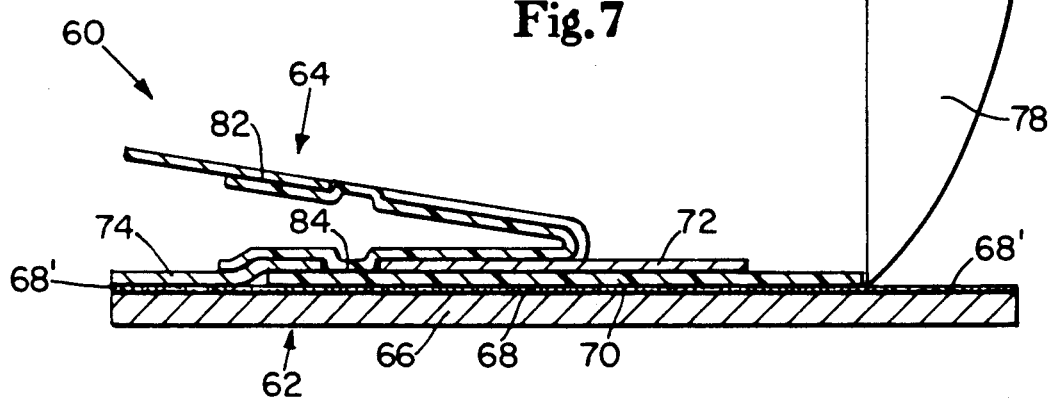
FIG. 7 is a schematic, cross-sectional view of the transdermal drug delivery device illustrated in FIG. 5 taken along section line B—B with the device's release tab shown partially peeled away from the device's lower subassembly.
Figure 8:
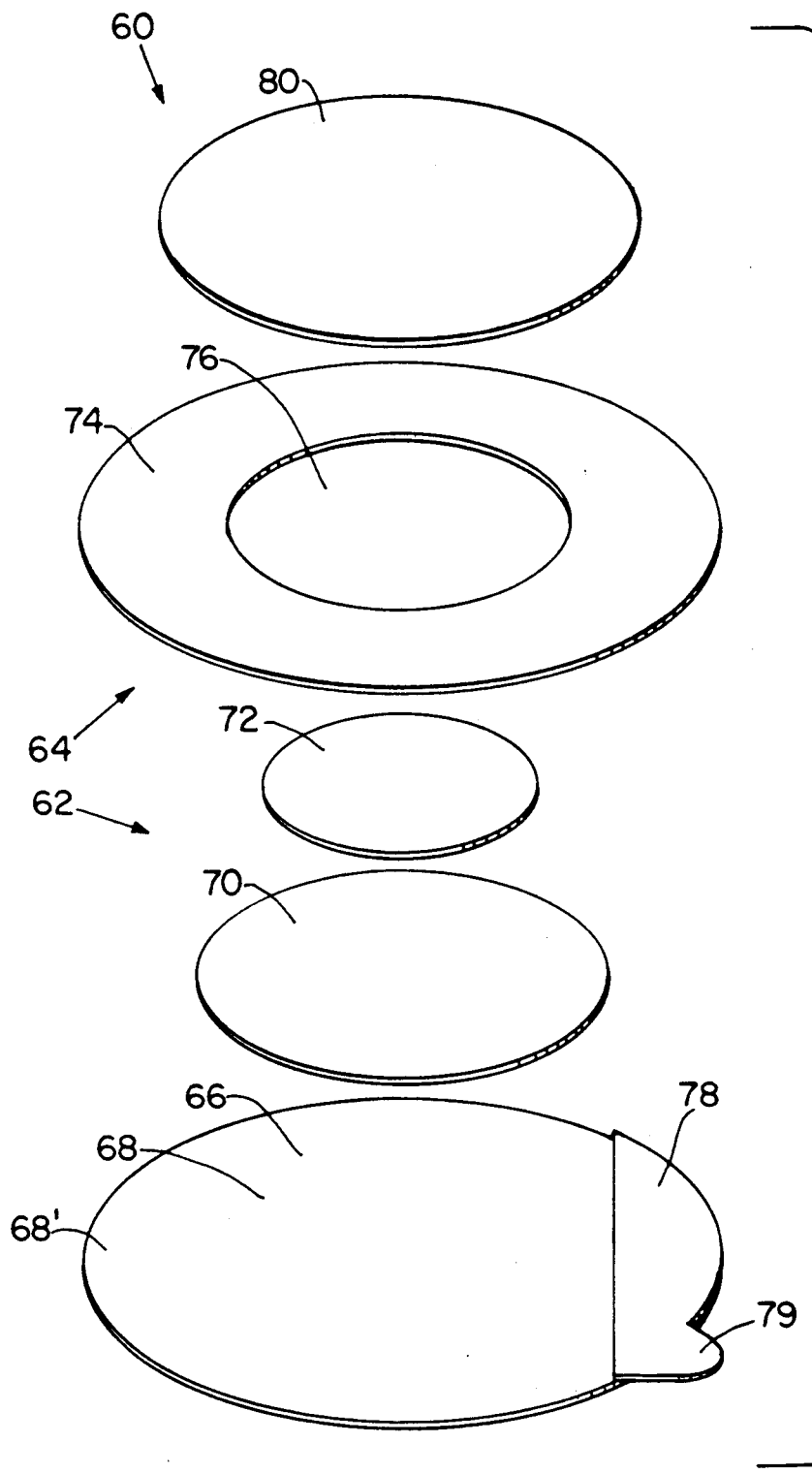
FIG. 8 is a schematic perspective, exploded view of the transdermal drug delivery device illustrated in FIGS. 5, 6, and 7.

Upper subassembly 64 also includes upper solvent/environment barrier film 80 whose bottom surface is firmly attached, e.g., heat-sealed, to the upper surface of release liner 74 where the two surfaces are in contact with each other as indicated as seal 82 in FIGS. 6 and 7. The middle portion of upper solvent/environment barrier film 80 extends through window 76 of release liner 74 and is hermetically sealed, e.g., heat-sealed, to lower solvent/environment barrier film 70 at seal 84 as shown in FIGS. 6 and 7. When sealed together, lower solvent/environment barrier film 70 and upper solvent/environment barrier film 80 form a hermetically-sealed compartment that contains drug reservoir 72.

As with the solvent barrier films and the hermetically-sealed compartment used in previously-described transdermal patch 10, lower solvent/environment barrier film 70 and upper solvent/environment barrier film 80 of patch 60 serve the critical functions of (1) protecting the drug formulation carried by reservoir 72 from common environmental factors such as moisture (water vapor), oxygen, and light, all of which either collectively or individually can adversely affect the stability and/or efficacy of the drug formulation; (2) establishing a hermetic seal that can be easily broken when the device is ready to be used on a patient; (3) maintaining the drug formulation separate from the device's perimeter adhesive during storage; and (4) preventing the drug formulation from permeating and being lost into other components of patch 60.

In a preferred embodiment of the present invention, lower solvent/environment barrier film 70 and upper solvent/environment barrier film 80 are made from a laminate comprised of a polyester such as polyethylene terephthalate (PET) as the outer layer and a modified, glycol-modified polyethylene terephthalate (PET-G) inner heat seal layer. Other suitable films which meet the definition of solvent/environment barrier film and from which film 70 and 80 can be made include the following laminates (from outside to inside): polyolefin/metalized PET/modified PETG; polyolefin/metal foil/modified PETG; polyolefin/tie/Barex ®, EVOH, nylon, or Selar ® PT/tie/modified PETG, and polyolefin/tie/polychlorotrifluoroethylene copolymer/tie/modified PETG.

The tie layer resins noted above are generally polyolefin-based, interlaminer bonding agents that are used to adhere incompatible layers together in laminated structures. The choice of a particular tie layer resin for a particular application depends on various factors such as the chemical nature of the materials being bonded, their melt viscosities, processing temperatures, and the type of laminating process and equipment being used. Examples of tie resins include the CXA family available from DuPont Chemical Company, which are essentially acid-anhydride modified ethylene vinyl acetate (EVA) multipolymers, and DuPont Elvax ® 3165 ethylene vinyl acetate copolymer. Other examples of tie layer resins include the Plexar ® family available from Northern Petrochemical Company, which include LDPE, MDPE, HDPE, PP, EVA copolymers.

The above-noted modified PET-G layers are particularly preferred because they exhibit excellent solvent barrier properties and yet are heat-sealable. However, the PETG layer used in lower film 70 and upper film 80 need not be the same. For example, a particularly preferred embodiment of patch 60 uses Presto PT-15-100 in lower film 70 and PT-20-100 in upper film 80, both of which are available from the Presto Products Company of Appleton, Wis., USA, to give permanently peelable heat seals with excellent solvent barrier properties. PT-15-100 is comprised of a PET film coextruded with a heat-seal layer which, when heat sealed to itself, provides permanently non-peelable seals. PT-20-100 is also a PET film coextruded with a heat seal layer which, when sealed to itself, provides permanelty peelable seals. In the preferred embodiment, PT-15-100 was chosen for lower solvent/environment barrier film 70 because polyester nonwoven reservoir 72 could be heat sealed to it to get a strong, solvent-resistant bond, PT-20-100 was chosen for upper solvent/environment barrier film 80 because it provided leak-tight, solvent-resistant heat seals to PT-15-100 was were permanently peelable.

The modified PET-G layer of solvent/environment barrier films 70 and 80 can be obtained by blending a PET-G such as Kodabond ® 5116 available from Eastman Chemicals with other polymeric materials such as polyethylene, ethylene vinyl acetate copolymers, ethylene ethyl acrylate copolymers, ethylene methylacrylate copolymers, ethylene acrylic acid copolymers, other polyesters and copolyesters, polystrene, and polystyrene copolymers. The additives transform a PET-G/PET-G heat seal from permanently unpeelable to one which is permanently peelable. The strength of the heat seal depends on both the nature and amount of the additive(s).

In use and with reference to FIG. 7, the user inserts his or her fingers between release liner 74 associated with upper subassembly 64, and release tab 78 associated with lower subassembly 62. Then, while having a firm grasp of upper subassembly 64 in one hand a"d lower subassembly 62 in the other, the user gently peels the two suoassemblies away from each other. In the process, hermetic seal 84 between lower barrier film 70 and upper barrier film 80 is gradually broken until upper subassembly 64 is fully separated from lower subassembly 62 and reservoir 72 is exposed. Finally, the user grasps portion 79 of release tab 44 and peels tab 44 away from lower subassembly 62 as shown in FIG. 7, thereby fully exposing adhesive coating 68' around the perimeter of coverstock 66. After subassemblies 62 and 64 have been fully separated from one another as just described, the user disposes of upper subassembly 64 in a proper manner and applies lower subassembly 62 directly to the patient's skin.

In some instances, it may be advantageous to maintain device 10 or 60 of the present invention in a sterile condition and/or to further protect device 10 or device 60 from common environmental factors by placing each device or a small group of devices within an outer protective overpouch or overwrap. Such overpouches or overwraps, which are commonly used in the medical industry to protect other types of bandages, gauzes, and instruments, can be made from a wide variety of materials and typically include at least one layer of a metal foil having graphics, instructions, etc. printed thereon.

EXAMPLE I

The following procedure describes an example of how to assemble transdermal drug delivery device 10 of the present invention, each device having an upper subassembly 14, a lower subassembly 12 that contains the drug formulation, and a hermetic seal joining the two subassemblies together.

In making lower subassembly 12, compartment bottom cover 26 was first made by using a paper cutter to cut a 6"×4" (15.2 cm×10.2 cm) sheet from a rollstock of skintone heat-sealable polyester film laminate, product number 1006 obtained from 3M Health Care Specialities, 6850 S. Harlem Ave., Bedford Park, Ill. USA. This laminate sheet was placed with its machine direction aligned with the long dimension of blades of an oval rule die and covered first with a piece of cardboard and then a piece of ¼" (0.64 cm) Lexan ®. The die was then placed in a Carver press and subjected to a pressure of 5000 psig which cut compartment bottom cover 26 from the sheet. Cover 26 was generally oval in shape, 5" (12.7 cm) long by 2 ¼" (5.7 cm) wide and having rounded ends, each with a 1 ⅛" (2.9 cm) radius.

Lower barrier film 20 of lower subassembly 12 was made by placing a 6"×4" (15.2 cm×10.2 cm) sheet of transparent Scotchpak ® heat-sealable polyester film laminate, product number 1220 also obtained from 3M Health Care Specialties, on the blades of a rule die, which was then covered with a piece of cardboard and a sheet of ¼" (0.64 cm) Lexan ®. The die was placed in a Carver press and subjected to a pressure of 5000 psig which cut lower barrier film 20 from the sheet. Lower barrier film 20 was generally oval in shape, 4" (10.2 cm) long by 1 ¼" (3.2 cm) wide and having rounded ends, each with a ⅝" (1.6 cm) radius.

Reservoir 16 was made by placing a 6"×4" (15.2 cm×10.2 cm) sheet of Reemay spunbonded polyester (style number 2011, basis weight 23 g/m$^2$, average thickness 6.5 mils (0.17 mm) obtained from Reemay Inc., P.0. Box 511, Old Hickory, Tenn., USA on the blades of a rule die which was then covered with a sheet of cardboard and Lexan ®. The die was placed in a Carver press and subjected to a pressure of 5000 psig which cut reservoir 16 from the polyester sheet. Reservoir 16 was generally oval in shape, 4 ¼" (10.8 cm) long by 1 ½" (3.8 cm) wide and having rounded ends, each with a ¾" (1.9 cm) radius.

To heat seal lower barrier film 20 to the inner surface of compartment bottom cover 26, a teflon-coated heat-sealing die with an oval perimeter 0.56" (1.4 cm) wide seal land was attached and registered to the top platen of a Sentinel heat sealer, model number 808, obtained from Packaging Industries, Hyannis, Mass., USA, which was set at 200° F. (93° C.), 80 psig, 4 second dwell. A piece of 70 durometer silicone rubber (1/32" thick) was placed on a puck designed to slide in and out from between the platens of the press. A cardboard template of the lower barrier film 20 was placed on the silicone rubber on the puck and aligned with the heat sealing die. Lower barrier film 20 was placed heat seal side up on the silicone rubber using the template for alignment. The barrier film template was removed and a template of compartment bottom cover 26 was placed on the puck and aligned with the heat sealing die. Compartment bottom cover 26 was then placed heat seal side down over lower barrier film 20 using the template for alignment, which was then removed from the puck. The puck was placed in the press which was energized and sealed lower barrier film 20 to compartment bottom cover 26.

The outer peripheral edge of reservoir 16 was heat-sealed to compartment bottom cover 26, which had been lined with lower barrier film 20 as just described. In attaching reservoir 16 to cover 26, a teflon-coated, heat-sealing die with an oval perimeter ⅛" (0.32 cm) wide seal land was attached and registered to the top platen of the press, which was set at 290° F. (143° C.), 40 psig, 1 second dwell. A cardboard template of reservoir 16 was placed on the puck and aligned with the heat sealing die. Reservoir 16 was placed on the puck using the template for alignment, which was then removed. A template of compartment bottom cover 26 was placed on the puck and aligned with the heat sealing die. Compartment bottom cover 26 was placed heat seal side down over reservoir 16 using the template for alignment, which was then removed from the puck. The puck was placed in the press which was energized and sealed the outer peripheral edge reservoir 16 to compartment bottom cover 26.

In making upper subassembly 14, compartment top cover 24 and upper barrier film 18 were cut from the same materials as used for compartment bottom cover 26 and lower barrier film 20, respectively, and also by using the same technique. Compartment top cover 24 was generally oval in shape, 5 ½" (14.0 cm) long by 2 ¾" (7.0) wide and having rounded ends, each with a 1.4" (3.5 cm) radius. Upper barrier film 18 was generally oval in shape, 4 ¼" (10.8 cm) long by 1 ½" (3.8 cm) wide and having rounded ends, each with a ¾" (1.9 cm) radius.

In making release liner 40 for upper subassembly 14, a sheet of 7"×4 ½" (17.8 cm×11.4 cm) cut from 3 pound (1.4 kg) poly-coated on one side and silicone-coated on the other release liner rollstock (product number 1361) obtained from 3M Health Care Specialties was aligned on the blades of a rule die and covered with cardboard and ¼" Lexan®. The die was placed in a Carver press and subjected to a pressure of 5000 psig which simultaneously cut aperture or window 42 in release liner 40 and liner 40 from the sheet. Window 42 was generally oval in shape, 4 ¾" (12.1 cm) long by 2" (5.1 cm) wide having rounded ends, each with a 1" (2.5 cm) radius. Release liner 40 was also generally oval in shape, 6 ¾" (17.2 cm) long by 4.0" (10.2 cm) wide having rounded ends, each with a 2.0" (5.1 cm) radius.

In attaching compartment top cover 24 to release liner 40, a teflon-coated heat sealing die with an oval perimeter 0.40" (1 cm) wide seal land was attached and registered to the top platen of the press, which was set at 290° F. (143° C.), 85 psig, 3 second dwell. Release liner 40 was placed on the puck with its silicone-coated side down and aligned with the heat sealing die. A cardboard template of compartment top cover 24 was placed on release liner 40 and also aligned with the sealing die. Compartment top cover 24 with its heat seal side down was aligned with the template, which was then removed from the puck. The puck was placed in the press which was energized and sealed compartment top cover 24 to release liner 40.

In attaching upper barrier film 18 to compartment top cover 24 (now attached to release liner 40), a teflon-coated heat sealing die with an oval perimeter ⅛" (0.32 cm) wide seal land was attached and registered to the top platen of the press, which was set at 200° F. (93° C.), 80 psig, 4 second dwell. A cardboard template of upper barrier film 18 was placed on the puck and aligned with the heat sealing die. Then, upper barrier film 18 was placed heat seal side up using the template for alignment which was then removed. Compartment top cover 24 was placed heat seal side down on upper barrier film. The puck was placed in the press which was energized to seal upper barrier film 18 to compartment top cover 24, which completed upper subassembly 14.

The buprenorphine gel was made in approximately a 700 gm batch via the following procedure. A 1 liter reaction flask with side indents for improved stirring and a fitted lid with four ports was used. The center port was equipped with a mechanical stirrer, while one side port contained a "Y" adapter which held a thermometer and a nitrogen outlet which was connected to a bubbler. A second side port housed the nitrogen inlet and also served as the addition port for raw materials. The third port was stoppered. Nitrogen flow was started through the reaction flask at a rate of 80-120 bubbles/min. The propylene glycol (95.6% w/w) was added with stirring, using a Lightning® mixer controlled by an external rheostat. The propylene glycol was then heated to 35° F. (95° C.) via a heating mantle. The hydroxypropyl cellulose (0.80% w/w) was added over about 10 minutes using a glass funnel with stirring (rheostat setting 30-40). When the hydroxypropyl cellulose addition was complete, the nitrogen inlet tube was replaced and the stir speed was increased to 50-60 (rheostat setting) and heat was applied to 100° C.±10° C. (212° F.). This temperature was maintained until the cellulose was completely dissolved and the solution was clear. At this point the heating mantle was removed and the solution was allowed to cool below 50° (122° F.) with stirring (rheostat setting 50-60). The methyl laurate (2.78% w/w) was added using a methyl laurate-wetted glass funnel with stirring (rheostat setting 40-50). This stir speed was maintained at room temperature for 12-18 hrs. Then the stir speed was increased (rheostat setting 60-70) and the solution was heated to 35°-40° C. (95°-104° F.). Slowly the buprenorphine (0.83% w/w) was added using a non-static glass funnel. The nitrogen inlet tube was replaced and the gel was heated (about hour) to 90°-95° C. (194°-203° F.) to dissolve the drug. A clear gel resulted when the drug was completely dissolved. At this point the heat was turned off, but the heating mantle was kept in place while the gel slowly cooled to room temperature. The gel was then transferred to a brown glass jar and blanketed with dry nitrogen before sealing with a solvent resistant screw cap.

With the use of a micro-pipette, 700 mg of the gel was applied to reservoir 16 area of lower subassembly 14. This step was carried out inside a glove box maintained at less than 10% relative humidity.

The final assembly of patch 10 consisted of heat-sealing lower subassembly 12 to upper subassembly 14 by forming hermetic seal 28 therebetween. A teflon-coated heat sealing die with an oval sealing land being 4.5" (11.43 cm) long, 1.75" (4.45 cm) wide and having a ⅞" (2.22 cm) radius on each rounded end, was attached and registered to the top platen of the press. The land width of this die was 0.040" (.1 cm). The press was set at 286° F. (140° C.)m, 65 psig and 0.7. second dwell. A cardboard template of lower subassembly 12 was placed on the puck and aligned with the heat sealing die. Lower subassembly 12 was placed heat seal side up on the puck using the template for alignment. The template was then removed. Upper subassembly 14 was then placed on the puck, heat seal side down, over lower subassembly 12 and aligned with the heat sealing die. The puck was then placed in the press and the press was activated to hermetically seal the subassemblies together.

A 7"×4.5" (17.78 cm×11.4 cm) sheet of PVC microfoam tape (product number 9772-L) obtained from 3M Health Care Specialties, was cut on a paper cutter. The release paper was removed and the coverstock was placed, adhesive side down, over compartment bottom cover 26 of the sealed subassemblies. This sheet was then placed on the blades of a rule die and aligned. It was covered with a piece of cardboard and a piece of ¼" (0.635 cm) Lexan ®. The die was then placed in a Carver Press and the pressure was increased to 5000 psig which cut complete patch 10 from the sheet. Patch 10 was approximately oval in shape with the dimensions being 6.75" (17.2 cm) long by 4.0" (10.2 cm) wide and having rounded ends, each with a 2" (5.1 cm) radius.

A pull tab was die cut from 3 lb. release liner, poly-coated one side, silicone-coated one side (product number 1361) obtained from 3M Health Care Specialties. This was applied to the patch by adhering the silicone-coated side to the adhesive on the coverstock on one of the rounded ends.

EXAMPLE II

The following procedure describes an example of how to assemble transdermal patch 60 of the present invention, each patch consisting of lower subassembly 62 which contained the drug formulation, upper subassembly 64, and hermetic seal 84 joining the two subassemblies together.

In making lower barrier film 70 of lower subassembly 62, a sheet of heat-sealable, polyester film laminate (product number PT-15-100) obtained from the Presto Products Company of Appleton, Wis., USA, was placed over the blades of a rule die and covered with a piece of cardboard and then a piece of ¼" (0.635 cm) Lexan ®. The die was placed in a Carver press and subjected to a pressure of 5000 psig which cut lower barrier film 70 from the sheet. Lower barrier film 70 was circular in shape and approximately 2 ¼" (5.72 cm) in diameter.

In making reservoir 72, a sheet of Reemay spunbonded polyester, (style number 2011, basis wt. 23 g/m², average thickness 6.5 mils) obtained from Reemay, Inc. was placed on the blades of a rule die and covered with a piece of cardboard and then a piece of ¼" (.635 cm) Lexan ®. The die was placed in a Carver press and subjected to a pressure of 5000 psig which cut reservoir 72 from the sheet. Reservoir 72 was circular in shape and approximately 1 7/16" (3.65 cm) in diameter).

To heat seal reservoir 72 to lower barrier film 70, a teflon-coated heat sealing die with a perimeter 0.108" (0.273 cm) wide seal land was attached and registered to the top platen of the press. The press was set at 325° F. (163° C.), 50 psig and 0.4 second dwell. A cardboard template of reservoir 72 was placed on the puck and aligned with the heat sealing die by using the template. The template was then removed and a template of lower barrier film 70 was placed on the puck and aligned with the heat sealing die. A lower barrier film 70 was placed heat seal side down over reservoir 72 using the template for alignment. The template was removed from the puck and lower barrier film 70 was then covered with a piece of 0.004" (0.10 cm) thick CHR Temp-R-Glass obtained from Cincinnati Gasket of Cincinnati, Ohio, USA. This was used to facilitate the release of components from the die. The puck was placed in the press and the press activated to seal reservoirs 72 to the compartment tops.

To begin making upper subassembly 64, a sheet of heat sealable, polyester film laminate (product number PT-20-100) also obtained from the Presto Products Company was placed over the blades of a rule die and covered with a piece of cardboard and then ¼" (0.635 cm) Lexan ®. The die was placed in a Carver press and subjected to a pressure of 5000 psig which cut upper barrier film 80 from the sheet. Upper barrier film 80 was circular in shape and approximately 2 9/16" (6.51 cm) in diameter.

A sheet of 3 lb. (1.4 kg) release liner, poly-coated on one side and silicone-coated on the other (product number 1361) obtained from 3M Health Care Specialties, was placed on the blades of a rule die and covered with a piece of cardboard and ¼" (0.64 cm) Lexan ®. The die was placed in a Carver press and subjected to a pressure of 5000 psig which simultaneously cut window 76 and release liner 74 from the sheet. Window 76 in release liner 74 was circular in shape and approximately 1 ⅞" (4.76 cm) in diameter. Release liner 74 was also circular in shape and approximately 3 7/16" (8.7 cm) in diameter.

To heat seal upper barrier film 80 to release liner 74, a teflon-coated sealing die with a perimeter 0.40" (1.0 cm) wide seal land was attached and registered to the top platen of the press. The press was set at 325° F. (163° C.), 50 psig and 3.0 second dwell. Release liner 74 was placed on the puck with its silicone-coated side down and aligned with the heat sealing die. A cardboard template of upper barrier film 80 was placed on release liner 74 and aligned with the heat sealing die. Upper barrier film 80 was placed heat seal side down using the template for alignment. The template was removed from the puck and upper barrier film 80 was then covered with a piece of 0.004" (.010 cm) thick CHR Temp-R-Glass. The puck was placed in the press and the press activated to seal upper barrier film 80 to window release liner 74. This completed upper subassembly 64.

The buprenorphine gel was made in accordance with the procedure described in Example I except that 88.76% w/w propylene glycol, 8.44% w/w methyl caprylate, 0.8% w/w hydroxypropyl cellulose, and 2.0% w/w buprenorphine were used. With the use of a micro-pipette, 300 mg of the gel was applied to reservoir 72 of lower subassembly 62.

The final assembly of patch 60 consisted of heat-sealing upper subassembly 64 to lower subassembly 62. A teflon-coated heat sealing die with a seal land being 0.045" (0.114 cm), with a 1.653" (4.19 cm) ID and 1.698" (4.31 cm) OD was attached and registered to the top platen of the press. The press was set at 350° F. (177° C.), 80 psig and 0.5 second dwell. A cardboard template of lower subassembly 62 was placed on the puck and aligned with the heat sealing die. Lower subassembly 62 with reservoir 72 was placed heat seal side up on the puck using the template for alignment. The template was then removed. Upper subassembly 64 was then placed on the puck, heat seal side down, over lower subassembly 62 and aligned with the heat sealing die. The puck was then placed in the press and the press was activated to seal the subassemblies together.

A 7"×9" (17.78 cm×22.86 cm) of PVC microfoam tape, (product number 9772-L) obtained from 3M Health Care Specialties, was cut on a paper cutter. The release paper was removed and the coverstock was placed, adhesive side down, over the bottom surface of lower barrier film 70. This sheet was then placed on the blades of a rule die and aligned. It was covered with a piece of cardboard and a piece of ¼" (0.635 cm) Lexan ®. The die was then placed in a Carver press and the pressure was increased to 5000 psig which cut complete patch 60 from the sheet. Patch 60 was circular in shape and approximately 3 7/16" (8.7 cm) in diameter.

A pull tab was die cut from 3 lb. release liner, polycoated one side, silicone-coated one side (product number 1361) obtained from 3M Health Care Specialties. This was applied to the patch by adhering the silicone-coated side to the adhesive on the coverstock.

While several particularly preferred embodiments of the present invention have been described and illustrated, it should now be apparent to those skilled in the art that various changes and modifications can be made without departing from the spirit and scope of the present invention. Accordingly, the following claims are intended to embrace such changes, modifications, and areas of application that are within the spirit and scope of this invention.

What is claimed is:

1. A storage-stable device for the transferal delivery of an active pharmaceutical, said device comprising:
   (a) a drug reservoir containing a mixtured of said pharmaceutical and a skin permeation enhancer, said reservoir having an upper surface and a lower surface;
   (b) a lower barrier film which is resistant to permeation by and absorption of said pharmaceutical and said skin permeation enhancer in contact with said lower surface of said reservoir;
   (c) an upper barrier film which is resistant to permeation by and absorption of said pharmaceutical and said skin permeation enhance in contact with said upper surface of said reservoir;
   (d) a compartment containing said drug reservoir and said lower and said upper barrier films, said compartment comprising a top cover located adjacent and secured to said upper barrier film and a bottom cover located adjacent and secured to said lower barrier film, each of said covers being comprised of a material which is resistant to permeation by moisture, oxygen and light, said top cover and aid bottom cover being hermetically sealed together smear their peripheral edges;
   (e) an outermost coverstock attached to said bottom cover of said outer compartment, said coverstock having an adhesive coating thereon, said hermetically-sealed compartment and said upper and lower barrier films together preventing said mixture of said pharmaceutical and said skin permeation enhancer from coming into contact with said adhesive coating on said outermost coverstock as well as the entry of moisture, oxygen and light from the surrounding environment into said reservoir; and
   (f) a release liner attached to said top cover of said compartment, said release liner being in contact with the periphery of said outermost coverstock, whereby peeling said release liner from said coverstock breaks said hermetic seal between said top cover and said bottom cover o said compartment, thereby exposing the adhesive at the periphery of said outermost coverstock and the upper surface of said drug reservoir.

2. The transdermal device recited in claim 1 further comprising:
   (g) a release tab interposed between said adhesive-coated coverstock and said release liner at an outer margin of said device.

3. The transdermal device recited in claim 1 further comprising:
   (h) a rate-controlling or nonrate-controlling membrane interposed between said reservoir and said upper barrier film.

4. The transdermal device recited in claim 1 wherein said upper and lower barrier films are made from a laminate comprised of an outer heat-sealable layer and an inner reservoir-contacting layer.

5. The transdermal device recited in claim 4 wherein said inner reservoir-contacting layer is made from a material selected from the group consisting of polyethylene terephthalate, fluorinated polyethylene terephthalate, a rubber modified acrylonitrile copolymer, nylon, EVOH, styrene acrylonitrile copolymer, polyvinylidine chloride copolymer, and polychlorotrifluoroethylene copolymer.

6. The transdermal device recited in claim 1 wherein said top cover and said bottom cover of said hermetically-sealed compartment are made from a laminate comprised of an outer heat-sealable layer, at least one intermediate environment barrier layer which is resistant to permeation by moisture, oxygen and light from the surrounding environment, and an inner heat-sealable layer.

7. The transdermal device recited in claim 6 wherein said environment barrier layer is selected from the group consisting of polyethylene terephthalate, metallized polyethylene terephthalate, metal foils, a polyvinylidine chloride copolymer, a rubber modified acrylonitrile copolymer, nylon, EVOH, and polychlorotrifluoroethylene copolymer.

8. A storage-stable device for the transdermal delivery of an active pharmaceutical, said device comprising:
   (a) a drug reservoir containing a mixture of said pharmaceutical and a skin permeation enhancer, said reservoir having an upper surface and a lower surface;
   (b) a lower barrier film, which is resistant to permeation by and absorption of said pharmaceutical and said skin permeation enhancer as well as resistant to permeation by moisture, oxygen and light, in contact with said lower surface of said reservoir;
   (c) an upper barrier film, which is resistant to permeation by and absorption of said pharmaceutical an said skin permeation enhancer as well as resistant to permeation by moisture, oxygen and light, in contact with said upper surface of said reservoir, said lower and said upper barrier films being hermetically sealed together near their peripheral edges;
   (d) an outermost coverstock attached to said lower barrier film, said coverstock having an adhesive coating thereon, said hermetically sealed lower and upper barrier films preventing said mixture of said pharmaceutical and said skin permeation enhancer from coming into contact with said adhesive coating on said outermost coverstock as well as the entry of moisture, oxygen and light from the surrounding environment into said reservoir; and (e) a release liner attached to said upper barrier film, said release liner being in contact with the periphery of said outermost coverstock, whereby peeling said release liner from said coverstock breaks said hermetic seal between said lower and said upper barrier films, thereby exposing the adhesive at the periphery of said outermost coverstock and the upper surface of said drug reservoir.

9. The transdermal device recited in claim 1 wherein said skin permeation enhancer is selected from the group consisting of polar solvent materials, polar lipid materials, and mixtures thereof.

10. The transdermal device recited in claim 9 wherein said polar solvent materials are selected from the group consisting of $C_3$–$C_4$ diols, $C_3$–$C_6$ triols, and mixtures thereof; and wherein said polar lipid materials are selected from the group consisting of fatty alcohols, fatty acids, fatty alcohol esters, fatty acid esters, and mixtures thereof.

11. The transdermal device recited in claim 9 wherein said polar solvent material is propylene glycol, and wherein said polar lipid material is methyl laurate or methyl caprylate.

12. The transdermal device of claim 9, claim 10 or claim 11, wherein said pharmaceutical is comprised of buprenorphine.

13. The transdermal device recited in claim 8 further comprising:

(f) a release tab interposed between said adhesive-coated coverstock and said release liner at an outer margin of said device.

14. The transdermal device recited in claim 8 further comprising:

(g) a rate-controlling or nonrate-controlling membrane interposed between said reservoir and said upper barrier film.

15. The transdermal device recited in claim 8 wherein said upper and said lower barrier films are made from a laminate comprised of an outer layer and an inner heat-sealable layer.

16. The transdermal device recited in claim 8 wherein said outer layer is made from a material selected from the group consisting of polyethylene terephthalate, metallized polyethylene terephthalate, polyvinylidine chloride copolymer, polychlorotrifluoroethylene copolymer, metal foil, polyolefins, metallized polyolefins, EVOH, nylon, rubber modified acrylonitrile copolymers, and multilaminate combinations thereof, and wherein said inner heat-sealable layer is a PET-G or modified PET-G.

17. The transdermal device of claim 18, claim 19 or claim 20, wherein said pharmaceutical is comprised of buprenorphine.

18. The transdermal device recited in claim 8 wherein said skin permeation enhancer is elected from the group consisting of polar solvent materials, polar lipid materials, and mixtures thereof.

19. The transdermal device recited in claim 8 wherein said polar solvent materials are selected from the group consisting of $C_3$–$C_4$ diols, $C_3$–$C_6$ triols, and mixtures thereof; and wherein said polar lipid materials are selected from the group consisting of fatty alcohols, fatty acids, fatty alcohol users, fatty acid esters, and mixtures thereof.

20. The transdermal device recited in claim 8 wherein said polar solvent material is propylene glycol, and wherein said polar lipid material is methyl laurate or methyl caprylate.

* * * * *

UNITED STATES PATENT AND TRADEMARK OFFICE
CERTIFICATE OF CORRECTION

PATENT NO. : 5,008,110

DATED : April 16, 1991

INVENTOR(S) : Arnold G. Benecke, Daniel J. Kinne, and Andrew J. Wnuk

It is certified that error appears in the above-identified patent and that said Letters Patent is hereby corrected as shown below:

Column 1, line 14, "inJection" should read -- injection --.

Column 14, line 13, after "film" insert -- 18 --.

Column 14, line 51, after "about" insert -- 1 --.

Column 17, line 34, "transferal" should read -- transdermal --.

Column 17, line 46, "enhance" should read -- enhancer --.

Column 17, line 55, "aid" should read -- said --.

Column 17, line 57, "smear" should read -- near --.

Column 18, line 6, "o" should read -- of --.

Signed and Sealed this

Thirteenth Day of July, 1993

Attest:

MICHAEL K. KIRK

Attesting Officer     Acting Commissioner of Patents and Trademarks